United States Patent [19]

Hines et al.

[11] Patent Number: 5,682,036

[45] Date of Patent: Oct. 28, 1997

[54] METHOD AND APPARATUS FOR ACCURATELY CALIBRATING AN ATTENUATION MAP FOR EMISSION COMPUTED TOMOGRAPHY

[75] Inventors: Horace H. Hines, San Jose; William K. Braymer, Pleasanton; John R. Liebig, San Jose, all of Calif.

[73] Assignee: ADAC Laboratories, Milpitas, Calif.

[21] Appl. No.: 580,843

[22] Filed: Dec. 29, 1995

[51] Int. Cl.$^6$ .................................................. G01T 1/166
[52] U.S. Cl. ........................... 250/363.09; 250/252.1
[58] Field of Search ..................... 250/363.09, 363.04, 250/363.07, 363.1, 252.1

[56] References Cited

U.S. PATENT DOCUMENTS 5,338,936  8/1994  Gullberg et al. ............... 250/363.04

OTHER PUBLICATIONS

Patrick Tan, et al., "A Scanning Line Source for Simultaneous Emission and Transmission Measurements in SPECT," The Journal of Nuclear Medicine, vol. 34, No. 10, pp. 1752–1758, Oct. 1993.

Primary Examiner—David P. Porta
Assistant Examiner—Richard Hanig
Attorney, Agent, or Firm—Blakely, Sokoloff, Taylor & Zafman LLP

[57] ABSTRACT

A method of calibrating an attenuation map for use in emission imaging in a gamma camera system. The attenuation map is generated using a transmission scan of the object of interest. The map includes a number of attenuation coefficients for the object. A computer program for generating the attenuation map includes an instruction for scaling the attenuation coefficients in the map from the transmission energy level to the emission energy level using a scaling factor. The scaling factor includes an effective attenuation coefficient for water, which is determined empirically. To determine the effective attenuation coefficient, the number of photons which pass from a transmission source through known depths of water using the emission energy level is counted. The effective attenuation coefficient is computed based on a standard equation describing the attenuation of photons by an absorber. The scaling factor used by the computer program is then set based on the effective attenuation coefficient.

21 Claims, 5 Drawing Sheets

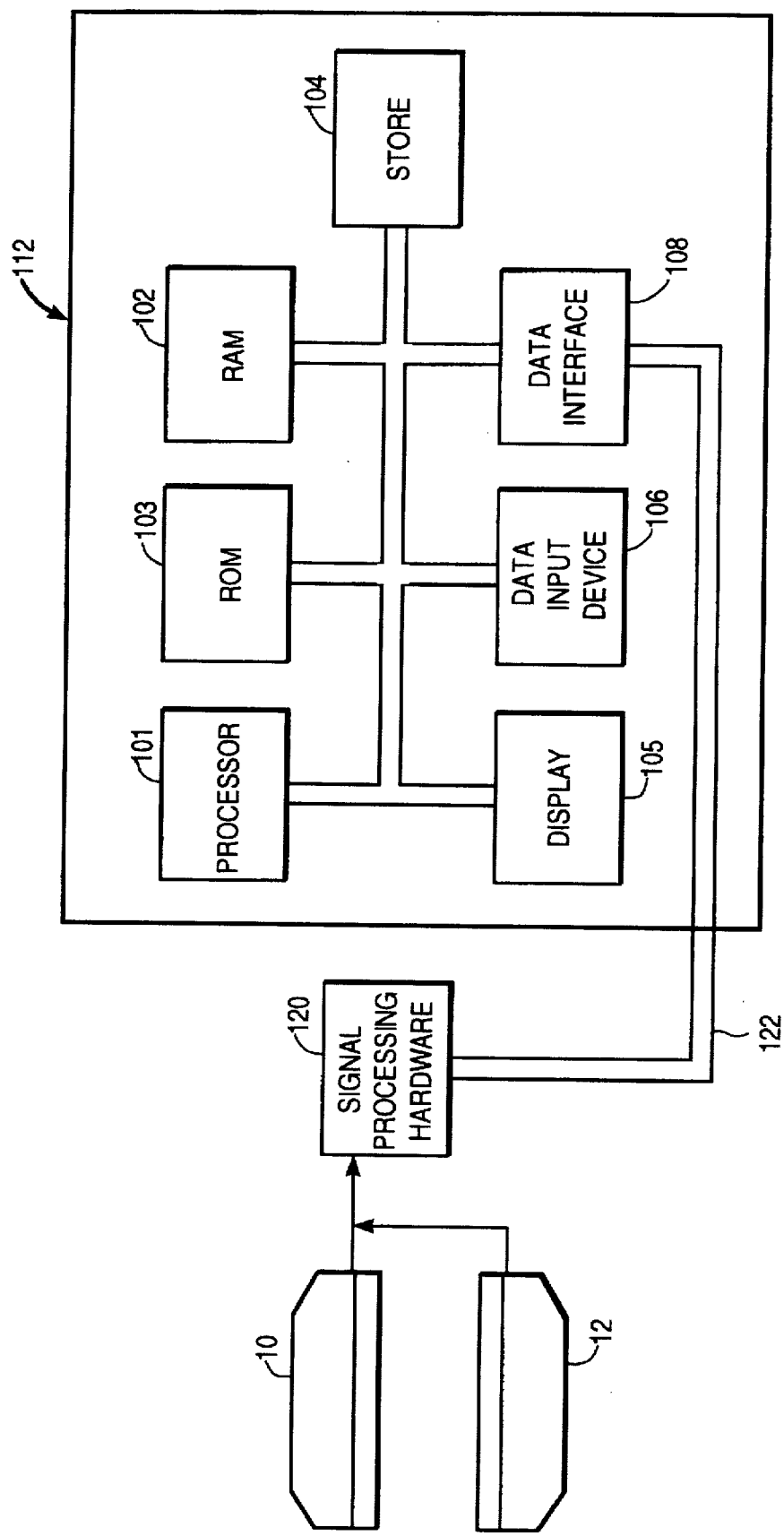

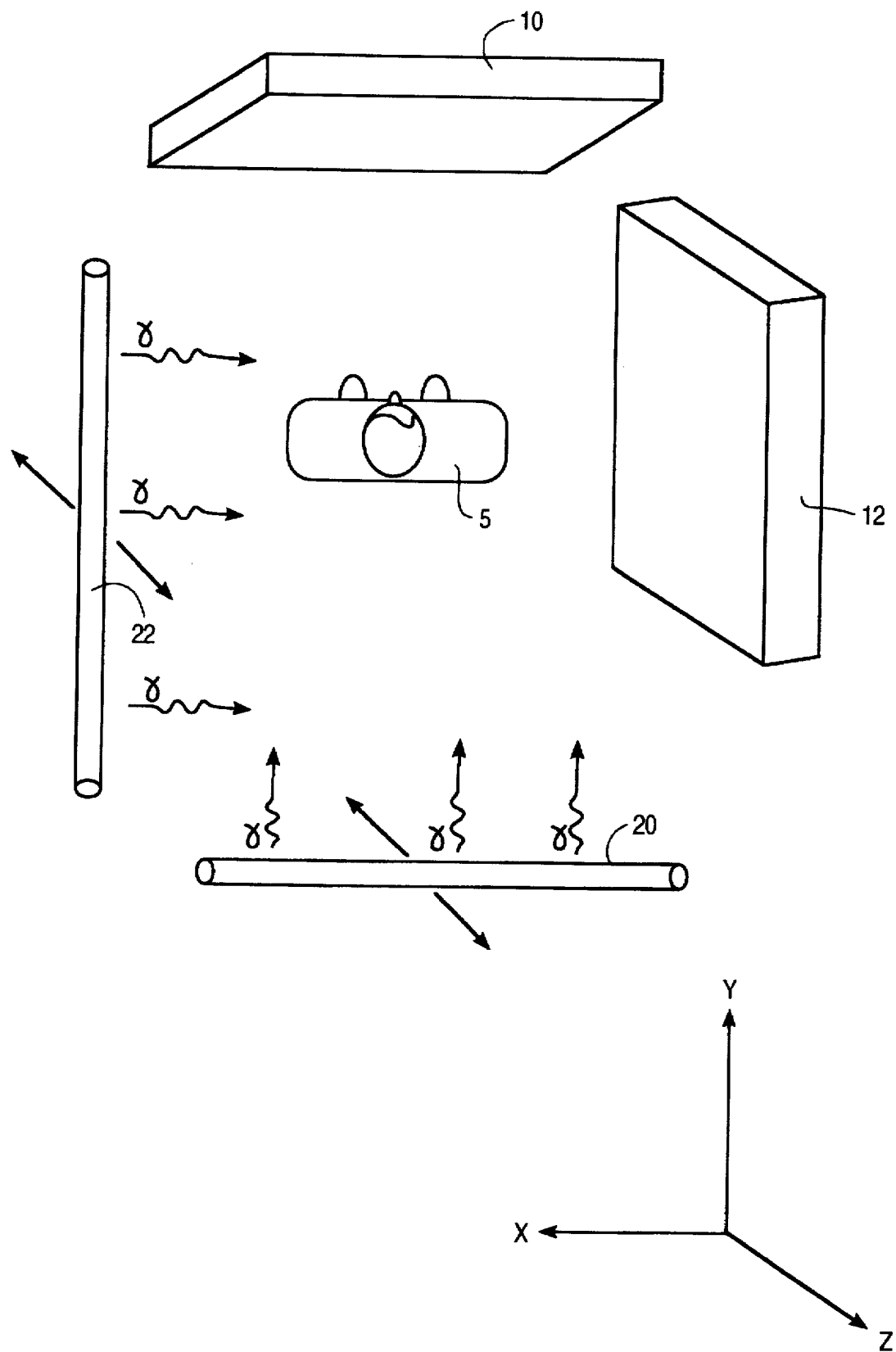
FIG_2

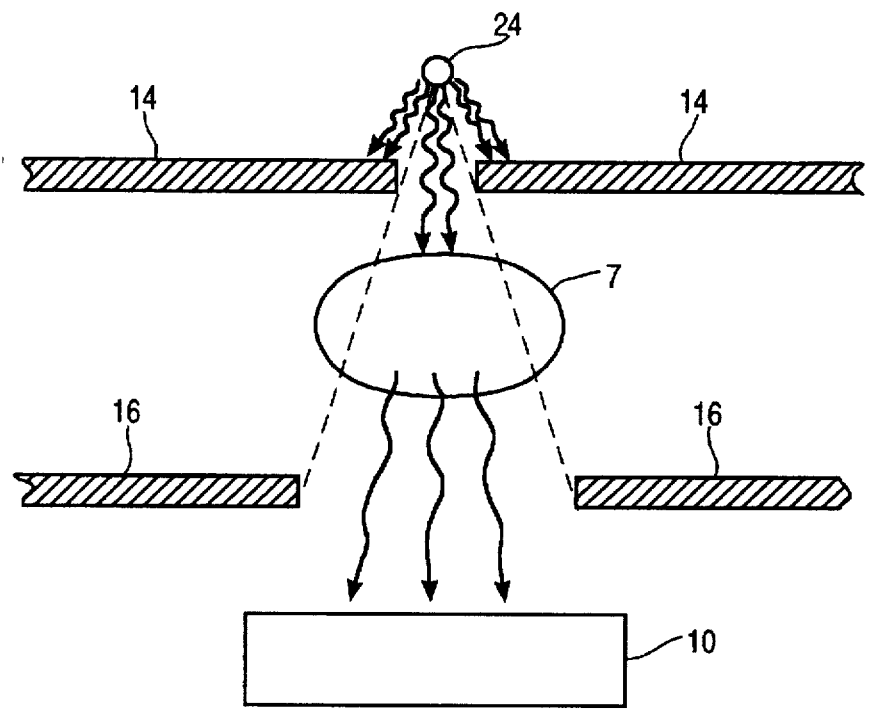
FIG_3
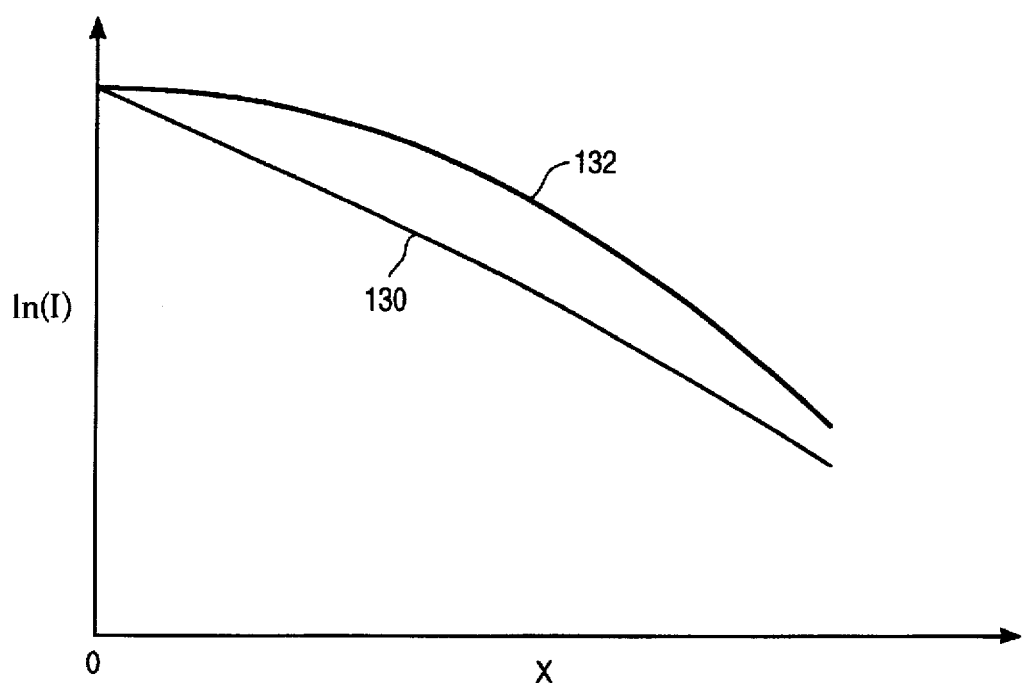
FIG_4

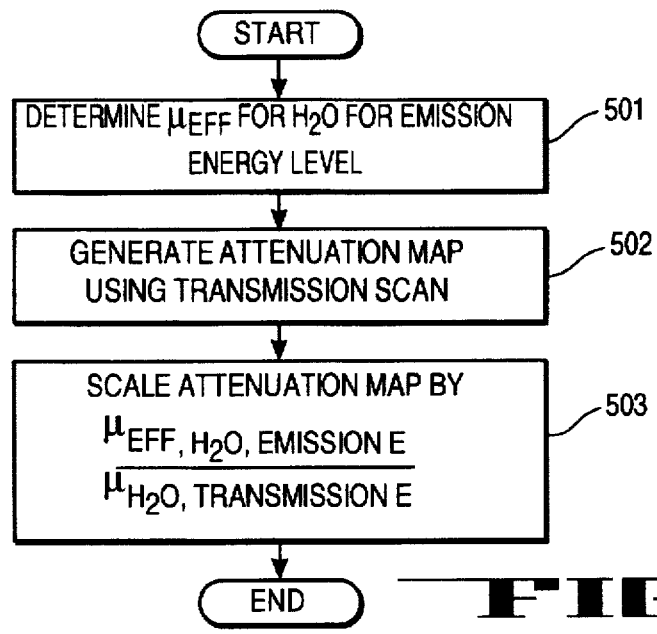
FIG_5
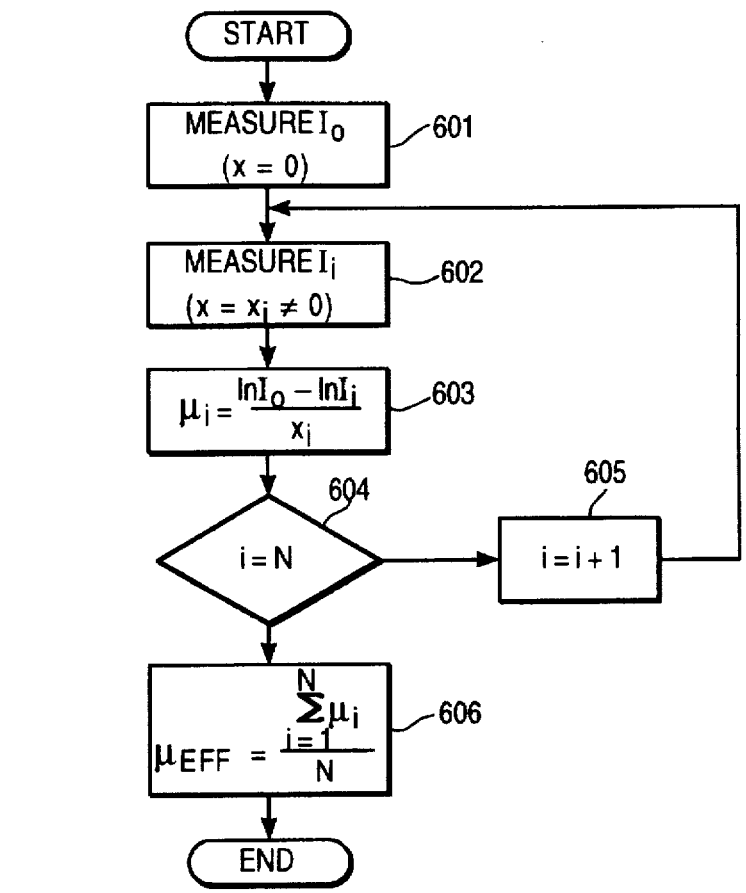
FIG_6

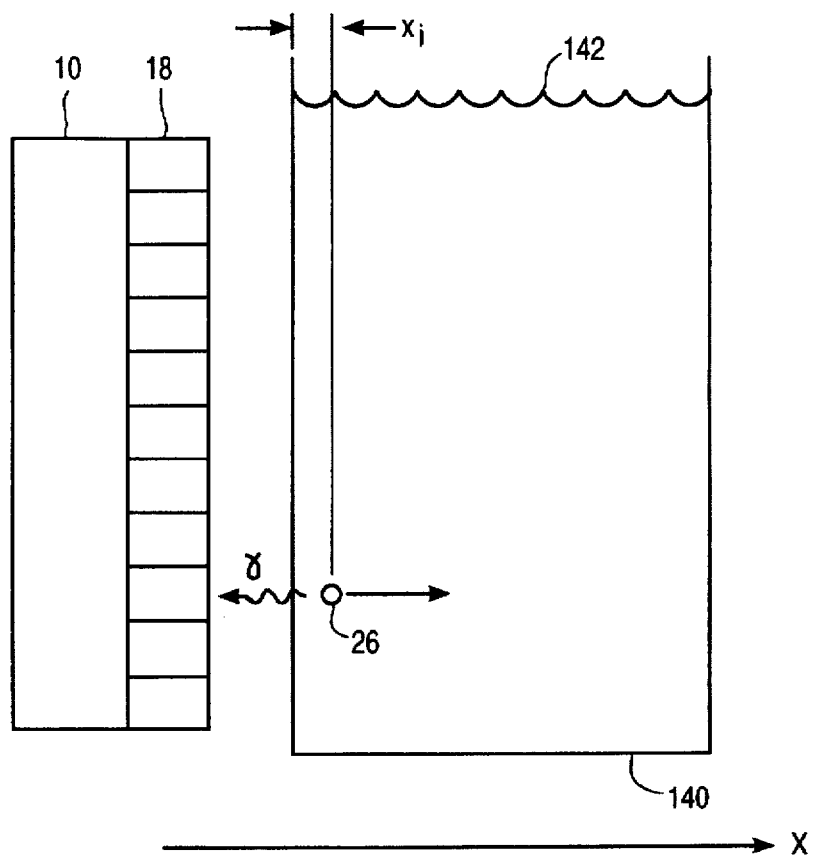
FIG_7
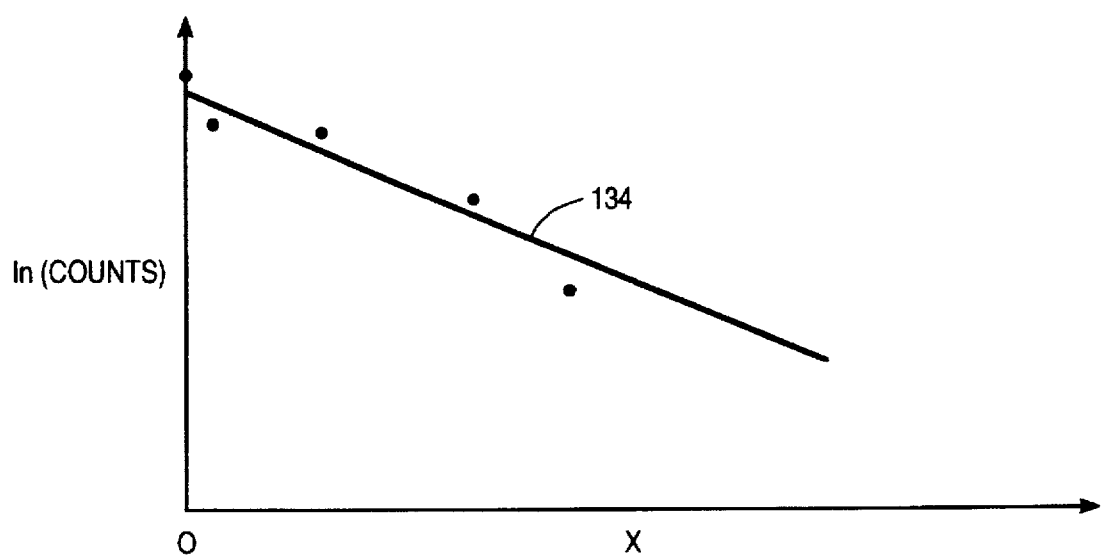
FIG_8

METHOD AND APPARATUS FOR ACCURATELY CALIBRATING AN ATTENUATION MAP FOR EMISSION COMPUTED TOMOGRAPHY

FIELD OF THE INVENTION

The present invention pertains to the field of nuclear medicine. More particularly, the present invention relates to calibrating a non-uniform attenuation map for emission computed tomography.

BACKGROUND OF THE INVENTION

In emission computed tomography (ECT), images of internal structures of the body are generated by injecting a patient with a radiopharmaceutical and then using a gamma camera to detect emitted gamma rays, or photons, from various angles around the body. Photons reaching a gamma camera's scintillation detectors produce scintillation events, which are detected by photomultiplier tubes and then converted by circuitry into electrical signals representing both position and energy information. These signals are then used to generate image data in a process known as reconstruction.

An effect known as photon attenuation is an important factor which affects the accuracy of images collected using ECT. Photon attenuation tends to degrade images by introducing image artifacts and other distortions that can result in false positive detection of lesions or the failure to detect lesions. Non-uniform photon attenuation creates image degradation by interfering with and partially absorbing the radiation emitted from an organ containing the radiopharmaceutical. Since each patient that is imaged using a gamma camera is different (different shape, different size, etc.), the tissue and bone structure surrounding an organ of interest are different for each patient. This surrounding tissue and bone structure attenuates the radiation emitted from a radiopharmaceutical distributed within the organ. The attenuation of the radiation is non-uniform because the attenuation coefficients of the different tissues and bone are different. Hence, radiation attenuation non-uniformly reduces the count density in the image. This attenuation can lead to falsely identifying an artifact when, in fact, healthy tissue is imaged and vice-versa.

Non-uniform attenuation caused by the body can be compensated for if an "attenuation map" of the body is known. An attenuation map contains a number of attenuation coefficient values corresponding to different points within the body. Transmission computed tomography is a technique which allows a gamma camera and a processing computer system to generate a non-uniform attenuation map of a particular object. Generally, during transmission scanning, radiation from a transmission source having known properties is transmitted through the patient and then detected by a scintillation detector. By knowing the intensity of the radiation transmitted by the source, and by measuring the intensity of radiation which passes through the object and is detected, a computer within the gamma camera system can determine the extent of non-uniform radiation attenuation over different parts of the body at different angles. From this information, a non-uniform attenuation map of the body can be determined using well-known methods and procedures. The non-uniform attenuation map is then used during the reconstruction process to correct emission image data collected during ECT imaging.

Transmission scanning and emission scanning are often performed at different energy levels to allow simultaneous acquisition. Consequently, the attenuation map, which is initially based on the transmission energy level, must be calibrated to the emission energy level in order to use the attenuation map to correct emission image data. For example, a transmission scan might be performed at an energy level of 100 kev using Gd-153, while the emission scan is performed using an energy level of 140 kev using Tc-99m. Calibration of the attenuation map generally involves scaling the coefficients of the attenuation map to correspond to the emission energy level. Calibration is performed by the computer in the gamma camera system executing computer program instructions that define the scaling operation. The use of an accurate scaling factor in calibrating the attenuation map is necessary for generating accurate emission images. However, for various reasons, the determination of an accurate scaling factor for calibration is problematic. One reason such a determination can be difficult is the scattering within the body of photons emitted from an organ of interest. Also, in practice, photons emitted by a given radiopharmaceutical are distributed over a narrow range of energy levels, rather than being confined to one precise energy level.

Therefore, it is desirable to provide for more accurate calibration of an attenuation map for use in correcting emission image data in ECT.

SUMMARY OF THE INVENTION

A method of calibrating an attenuation map for use in a gamma camera system is described. The attenuation map includes a number of attenuation coefficients for an object of interest. In the method, machine instructions for generating the attenuation map are provided. The machine instructions include a scaling factor for scaling the attenuation coefficients to a predetermined energy level. An effective attenuation coefficient is determined empirically for an attenuating medium representative of the object of interest. The scaling factor is then set based on the effective attenuation coefficient.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which:

FIG. 1 is a block diagram of a gamma camera system.

FIG. 2 illustrates portions of a gamma camera system configured for performing a transmission scan of a patient.

FIG. 3 illustrates conceptually a narrow-beam geometry for measurement of photon attenuation.

FIG. 4 is a graph showing a comparison of photon attenuation in narrow-beam and broad-beam geometries.

FIG. 5 is a flowchart illustrating a routine for calibrating an attenuation map.

FIG. 6 is a flowchart illustrating a routine for empirically determining an attenuation coefficient for use as a scaling factor.

FIG. 7 illustrates a configuration for measuring an effective attenuation coefficient for water.

FIG. 8 is a graph illustrating sample data points obtained in measuring an effective attenuation coefficient for water.

DETAILED DESCRIPTION

A method and apparatus for accurately calibrating an attenuation map for ECT are described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention.

FIG. 1 illustrates a gamma camera system which may be used in accordance with the present invention. The gamma camera system includes a general purpose computer system 112 used by the present invention for processing image information supplied from scintillation detectors 10 and 12. The general purpose computer system 112 is capable of performing image processing functions (e.g., processing of emission and transmission data). The computer system 112 also controls movement of detectors 10 and 12 on a gantry and controls motion controllers for controlling the movement of transmission line sources, which are discussed below.

The computer system 112 includes an address/data bus 100 for communicating information within the system; a central processing unit (CPU) 101 coupled to the bus 100 for executing instructions and processing information; a random access memory (RAM) 102 coupled to the bus 100 for storing information and instructions for the central processor 101; a read only memory (ROM) 103 coupled to the bus 100 for storing static information and instructions for the processor 101; a mass storage device 104 coupled to the bus 100 for storing image information and instructions; a display device 105, such as a cathode ray tube (CRT), coupled to the bus 100 for displaying information to computer user; an alphanumeric input device 106 including alphanumeric and function keys coupled to the bus 100 for communicating information and command selections to the central processor 101; a cursor control device (part of the data input device 106) coupled to the bus for communicating user input information and command selections to the central processor 101; and, a data interface device 108 coupled to the bus 100 for communicating command selections to the processor 101. A hardcopy device (e.g., printer) may also be coupled to bus 100.

The display device 105 of FIG. 1 utilized with the computer system 112 of the present invention may be a liquid crystal device, cathode ray tube (CRT), or other display device suitable for creating graphic images and alphanumeric characters recognizable to the user. The cursor control device allows the computer user to dynamically signal the two dimensional movement of a visible symbol (pointer) on a display screen of the display device 105. Many implementations of the cursor control device are known in the art including a trackball, finger pad, mouse, joystick or special keys on the alphanumeric input device 105 capable of signaling movement of a given direction or manner of displacement. The mass storage device 104 may be a magnetic or optical disk and disk drive or other similar device.

The computer system 112 interfaces with scintillation detectors 10 and 12 via signal processing hardware circuits 120 over bus 122. The signal processing hardware 120 comprises amplification circuitry and analog-to-digital conversion circuits for converting channel signals from the detectors to digital data for transmission to the computer system 112. In particular, signal processing hardware 120 converts the outputs of photomultiplier tubes in detectors 10 and 12 into spatial coordinate data and energy data for detected scintillation events.

Transmission and emission data are stored in memory 102 in matrix form. Separate matrices may be used to store transmission and emission data, respectively. Nonuniform attenuation maps derived from transmission scanning are also stored in memory 102 in matrix form. Each cell, or "bin", of a matrix corresponds to one pixel in an output image. Once image matrices are collected at different ECT angles, tomographic reconstruction is performed to generate multiple slice images or a three-dimensional image of an organ.

FIG. 2 shows portions of a gamma camera system configured to perform a transmission scan of a patient 5. Data acquired using the transmission scan may be used to generate an attenuation map for correcting emission data. In performing the transmission scan, scintillation detectors 10 and 12 are positioned in a 90° orientation, as shown in FIG. 2. Transmission line sources 20 and 22 are used to transmit gamma radiation through the patient 5 to detectors 10 and 12, respectively. For various different angles about the Z axis, line sources 20 and 22 are translated across the fields-of-view of detectors 10 and 12, respectively. Detectors 10 and 12 measure the amount of radiation from line sources 20 and 22, respectively, which passes completely through the patient 5. Using this configuration, transmission scanning may be performed simultaneously with emission scanning, provided different energy levels are assigned for the emission and transmission scans.

In general, attenuation of photons within an absorber can be described by the following equation:

$$I = I_0 e^{-\mu x} \quad (1)$$

where:

I represents the intensity of the photon beam transmitted through a thickness x of the absorber;

$I_0$ represents the intensity recorded with no absorber present;

μ represents the linear attenuation coefficient of the absorber at the photon energy level of interest; and x represents the thickness of the absorber through which the photons pass.

Equation (1) generally holds true for a "narrow-beam geometry", an example of which is illustrated conceptually in FIG. 3. In a narrow-beam geometry, photons from a source 24 are collimated using a narrow-aperture source collimator 14. The photons pass through an absorber 7 and then through a detector collimator 16 before reaching a detector 10. The value of the attenuation coefficient μ for an absorber can be obtained graphically by plotting In(I) vs. x. Referring now to FIG. 4, the resulting plot for a true narrow-beam geometry, is a line 130, such that the magnitude of the line's slope equals the attenuation coefficient μ.

In practice, however, the actual geometry involved when imaging a patient is not a true narrow beam geometry. In the absence of a narrow-beam geometry, there is significant scattering within the body of photons emitted by an organ of interest during emission imaging. As a result of such scattering and other factors, the plot of In(I) vs. x in such a geometry is not linear and more closely resembles curve 132 of FIG. 4. This lack of linearity reflects the fact that the actual attenuation coefficient μ in such a case is not constant for the absorber (i.e., for the body). Rather, the attenuation coefficient μ varies as a function of x. Consequently, the use of an accepted, "textbook" value of the attenuation coefficient μ in the scaling factor for calibrating an attenuation map may result in the generation of artifacts in the final output images because of variations in μ, as will be discussed below.

As noted above, transmission scanning and emission scanning are generally performed simultaneously by assigning a different energy level for the transmission scan than for the emission scan. Because the attenuation map is generated from the transmission scan, the attenuation map is initially calibrated to the energy level used for the transmission scan. Consequently, the attenuation map must be scaled to the energy level used for the emission scan in order to use the map to correct emission data. That is, the values in the matrix which forms the attenuation map are multiplied by a scale factor. In performing the scaling operation, the processor 101 of the gamma camera system executes computer program code containing one or more instructions that define the scaling operation. The value of the scaling factor may be included in these instructions prior to execution of the code, or the value (or any component thereof) may be read in as a data value and then computed during execution.

One possible approach to determining a scaling factor is to, first, identify a substance that has a composition similar to that of the object of interest (i.e., the patient), and to then base the scaling factor upon "textbook" values of the attenuation coefficient μ for that substance. For example, because the human body is composed mostly of water, the attenuation coefficient of water $\mu_{H_2O}$ may be used as an approximation of the attenuation coefficient of the human body. Therefore, the scaling factor K might be taken to be the ratio of the attenuation coefficient of water $\mu_{H_2O}$ at the emission energy level to the attenuation coefficient of water $\mu_{H_2O}$ at the transmission energy level, as shown in equation (2).

$$K = \frac{\mu_{H_2O,EmmissionE}}{\mu_{H_2O,TransmissionE}} \quad (2)$$

Textbook values of $\mu_{H_2O}$ for use in equation (2) are available for different energy levels from numerous well-known sources. Although the scaling factor K of equation (2) might seem to be a logical choice, in actual practice such a scaling factor tends to produce disappointing results. In particular, because of scattering of photons within the human body and the distribution of photons over a range of energy levels, such a scaling factor proves to be inaccurate, causing image artifacts to be generated. Therefore, in accordance with the present invention, this problem is solved by first determining an effective attenuation coefficient for water $\mu_{EFF,H_2O}$ for an emission energy level, and then using the effective attenuation coefficient, rather than textbook values attenuation coefficient, in the scaling factor used to scale the attenuation map. Hence, a scaling factor K' is used according to the present invention and is computed according to equation (3).

$$K' = \frac{\mu_{EFF,H_2O,EmissionE}}{\mu_{H_2O,TransmissionE}} \quad (3)$$

FIG. 5 shows the overall routine for calibrating an attenuation map according to the present invention. For purposes of illustration, assume an energy level of 72 keV is selected for emission scanning using Tl-201, whereas an energy level of 100 keV is selected for transmission scanning using Gd-153 sources. It should be appreciated, however, that the practice of the present invention is not limited to any specific energy levels. Referring to FIG. 5, an effective attenuation coefficient $\mu_{EFF,H_2O}$ is determined for water for the emission energy level (step 501). An attenuation map is then generated using a transmission scan at the transmission energy level (step 502). Then, the attenuation map is scaled to the emission energy level by multiplying the coefficient values of the attenuation map by the scaling factor K' of equation (3) (step 503).

In accordance with the present invention, the effective attenuation coefficient $\mu_{EFF,H_2O}$ is determined empirically by using the test configuration of FIG. 7 to acquire radiation count data. Referring to FIG. 7, a container 140 is filled with water 142. A scintillation detector 10 with a collimator 18 is placed next to the container 140. First, the intensity $I_o$ of photons emitted from a radiation source 26 is measured in terms of counts by placing the source 26 next to the detector 10 (step 601). The source 26 is selected such that its energy level equals the energy level which will be used for emission scanning during imaging of a patient. Therefore, given the illustrative energy levels assumed above, the source 26 would be selected to have an energy level of 72 keV, which is the desired emission energy level. Next, a container 140 is placed next to the detector 10, and the source 26 is submerged in the water 142. It is preferable that the size and positioning of the container 140 relative to the detector 10 be sufficiently large, such that the container 140 effectively overlaps completely the field of view of the detector 10. The intensity $I_i$ of photons passing through the water 142 is then measured in terms of counts for a number of different values of x (i.e., $x_i$), as shown in FIG. 7, (step 602).

It is preferable that four or more values of $x_i$ be used to measure $I_i$. Further, the range of values of $x_i$ need only reflect the range of distances which photons are likely to travel within the human body; therefore, a range of $x_i$ of from 0 to approximately 20 centimeters with an increment of 5 centimeters or less between values of $x_i$ should be sufficient.

Various methods may be used to determine the value of the effective attenuation coefficient $\mu_{EFF,H_2O}$ from the acquired count data. FIG. 6 illustrates one such method. In the routine FIG. 6, the value of $\mu_{EFF,H_2O}$ is determined according to equation (4) (step 606), where $\mu_i$ is defined by equation (5) (step 603).

$$\mu_{EFF,H_2O} = \frac{\sum_{i=1}^{N} \mu_i}{N} \quad (4)$$

where:

$$\mu_i = \frac{\ln I_0 - \ln I_i}{x_i} \quad (5)$$

Another method of determining $\mu_{EFF,H_2O}$ using the test setup of FIG. 7 is to determine a best fit line of datapoints representing ln(I) for various values of x. The magnitude of the slope of the best fit line will then represent the value of the effective attenuation coefficient $\mu_{EFF,H_2O}$ of water at the emission energy level. FIG. 8 shows a sample plot of ln(I) (measured in counts) for various values of x acquired using the test setup of FIG. 7. A best fit line 134 may be determined by use of a linear regression formula, which is well-known, or by visually plotting a best fit line 134.

Thus, in accordance with the present invention, the scaling factor K' of equation (3), which incorporates an effective attenuation coefficient $\mu_{EFF,H_2}O$, is used to scale an attenuation map to an emission energy level, rather than the scaling factor K of equation (2), which makes use of textbook values of $\mu_{H_2O}$. As a result, the final output images obtained are of higher quality, since the scaling factor employed is more accurate.

Thus, a method and apparatus for accurately calibrating an attenuation map for ECT have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of enabling calibration of an attenuation map of a patient by a gamma camera system capable of generating the attenuation map and scaling the attenuation map to a predetermined energy level, the method comprising the steps of:
   empirically determining an effective attenuation coefficient for an attenuating medium representative of the patient; and
   setting a scaling factor based on the empirically-determined effective attenuation coefficient, wherein the scaling factor is for application by the gamma camera system to the attenuation map of the patient to scale the attenuation map of the patient to the predetermined energy level.

2. A method according to claim 1, wherein the determining step comprises the steps of:
   for each of a plurality of thicknesses of the attenuating medium, transmitting photons from a transmission source through said thickness of the attenuating medium;
   for each of said thicknesses, counting the number of photons transmitted by the transmission source that pass completely through said thickness of the attenuating medium; and
   determining the effective attenuation coefficient based on the counting step.

3. A method according to claim 2, wherein the attenuating medium is water.

4. A method according to claim 1, wherein the determining step comprises the steps of:
   for each of said thicknesses of said attenuating medium, calculating the natural log (ln) of the number of photons counted in said counting step;
   associating each of said natural logs with the corresponding thickness to establish a relationship between said natural logs and said thicknesses, wherein said relationship is characterized by a line;
   determining a slope of the line, the slope having a magnitude; and
   establishing the effective attenuation coefficient as the magnitude of the slope of the line.

5. A method according to claim 1, further comprising the steps of:
   operating the gamma camera system to generate the attenuation map of the patient; and
   operating the gamma camera system to scale the attenuation map of the patient to the predetermined energy level by applying the scaling factor to the attenuation map.

6. A method according to claim 1, wherein the scaling factor comprises a ratio of the effective attenuation coefficient to a predetermined attenuation coefficient, the effective attenuation coefficient corresponding to an emission imaging energy level, the predetermined attenuation coefficient corresponding to a transmission imaging energy level.

7. A method of enabling calibration of an attenuation map by a gamma camera system, the method comprising the steps of:
   determining an effective attenuation coefficient for an absorptive medium representative of an object to be imaged, wherein the determining step includes the steps of:
   positioning a transmission source at at least one position within the absorptive medium;
   counting a number of photons transmitted from the transmission source through the absorptive medium from each of said at least one position within the absorptive medium; and
   determining the effective attenuation coefficient based on results of the counting step; and
   generating a scaling factor based on the effective attenuation coefficient, the scaling factor for scaling the attenuation coefficients from a first energy level to a second energy level.

8. A method according to claim 7, wherein the absorptive medium is water.

9. A method according to claim 8, wherein the scaling factor comprises a ratio of the effective attenuation coefficient to a second attenuation coefficient for the absorptive medium, the effective attenuation coefficient corresponding to an emission energy level, the second attenuation coefficient corresponding to a transmission energy level.

10. A method according to claim 7, further comprising the step of scaling the attenuation map based on the scaling factor to generate a calibrated attenuation map.

11. A method according to claim 7, wherein the determining step comprises the steps of:
   for each of said positions, calculating the natural log (ln) of the number of photons counted in said counting step;
   associating each of said natural logs calculated in the calculating step with a corresponding position to determine a relationship between said number of photons and said positions, wherein said relationship is characterized by a line;
   determining a slope of the line; and
   computing the effective attenuation coefficient based on the slope of the line.

12. A method according to claim 7, wherein the effective attenuation coefficient ($\mu_{eff}$) is computed according to the equation:

$$\mu \text{eff} = \frac{\sum_{i=1}^{N} \mu_i}{N} \text{ wherein } \mu_i = \frac{\ln(I_o) - \ln(I_i)}{x_i};$$

and wherein
   $I_i$ represents the number of photons counted with the transmission source positioned at the ith position within the absorptive medium;
   $I_o$ represents the number of photons counted in the absence of the absorptive medium;
   $x_i$ represents the thickness of the absorptive medium associated with the ith position; and
   N represents the number of positions within the absorptive medium used in the counting step.

13. A method of providing an attenuation map of an object, the attenuation map for use in a nuclear camera imaging system, the method comprising the steps of:
   controlling a radiation source to transmit radiation through the object;
   detecting the radiation transmitted through the object;
   detecting emission radiation emitted from the object, the emission radiation having an emission energy level;
   generating a plurality of attenuation coefficients based on the detected radiation transmitted through the object;
   determining a scaling factor based on a previously-determined effective attenuation coefficient of an attenuator representative of the object, the effective attenuation coefficient corresponding to the emission energy level, wherein the effective attenuation coefficient is experimentally-determined; and scaling the attenuation coefficients to the emission energy level based on the scaling factor to generate a scaled attenuation map.

14. A method according to claim 13, further comprising the step of determining the effective attenuation coefficient, wherein the determining step includes the steps of:

transmitting radiation from a transmission source through each of a plurality of thicknesses of the attenuator;

for each thickness of the attenuator, detecting the amount of radiation transmitted by the transmission source which passes through said thickness of the attenuator; and determining the effective attenuation coefficient based on the detected amount of radiation transmitted by the transmission source which passes through said thickness of the attenuator.

15. A method according to claim 12, wherein the attenuator is water.

16. A method according to claim 11, wherein the step of computing the scaling factor comprises the step of computing the ratio of the effective attenuation coefficient to a predetermined attenuation coefficient for the attenuator, the predetermined attenuation coefficient corresponding to an energy level of the radiation transmitted through the object by the radiation source.

17. A method according to claim 13, wherein the step of determining the effective attenuation coefficient comprises the step of computing the effective attenuation coefficient ($\mu_{\mathit{eff}}$) according to the equation:

$$\mu\text{eff} = \frac{\sum\limits_{i=1}^{N} \mu_i}{N} \quad \text{wherein} \; \mu_i = \frac{\ln(I_o) - \ln(I_i)}{x_i} \; ;$$

and wherein $I_i$ represents the amount of detected radiation transmitted through the ith thickness of the attenuator;

$I_o$ represents amount of detected radiation detected in the absence of the attenuator;

$x_i$ represents the value of the ith thickness of the attenuator; and

N represents the total number of thicknesses of the attenuator in the detecting step.

18. An apparatus for generating images of an object, the apparatus comprising:

a detector for detecting radiation at either a first energy level or a second energy level and generating image information in response thereto;

a radiation source for transmitting radiation at the first energy level through the object to the radiation detector;

a memory;

a processor coupled to receive the image information, coupled to control the radiation source, and coupled to the memory, wherein the processor is configured to generate and store in the memory an attenuation map based on the radiation transmitted through the object, wherein the attenuation map includes a plurality of attenuation coefficients for the object; and wherein the processor is further configured to scale the attenuation map by scaling the attenuation coefficients to the second energy level based on an effective attenuation coefficient of an absorptive medium representative of the object at the second energy level, wherein the effective attenuation coefficient is experimentally-determined.

19. An apparatus according to claim 18, wherein the absorptive medium is water.

20. An apparatus according to claim 18, wherein the effective attenuation coefficient is determined according to a method comprising the steps of:

for each of a plurality of thicknesses of the absorptive medium, transmitting radiation from a transmission source from a point within the absorptive medium through said thickness of the absorptive medium;

for each of said thicknesses, detecting the amount of radiation transmitted by the transmission source which passes through said thickness of the attenuator; and determining the effective attenuation coefficient based on the detected amount of radiation which passes through said plurality of thicknesses of the absorptive medium.

21. An apparatus according to claim 20, wherein the effective attenuation coefficient ($\mu_{\mathit{eff}}$) is computed according to the equation:

$$\mu\text{eff} = \frac{\sum\limits_{i=1}^{N} \mu_i}{N} \quad \text{wherein} \; \mu_i = \frac{\ln(I_o) - \ln(I_i)}{x_i} \; ;$$

and wherein $I_i$ represents the number of photons counted which pass through the ith thickness of the absorptive medium;

$I_o$ represents the number of photons counted in the absence of the absorptive medium;

$x_i$ represents the ith thickness of the absorptive medium; and

N represents the number of values of thicknesses of the absorptive medium used in the step of detecting the amount of radiation.

\* \* \* \* \*